United States Patent [19]
Goble

[11] Patent Number: 6,093,186
[45] Date of Patent: Jul. 25, 2000

[54] ELECTROSURGICAL GENERATOR AND SYSTEM

[75] Inventor: Colin C. O. Goble, Penarth, United Kingdom

[73] Assignee: Gyrus Medical Limited, Cardiff, United Kingdom

[21] Appl. No.: 08/993,929

[22] Filed: Dec. 18, 1997

[30] Foreign Application Priority Data

Dec. 20, 1996 [GB] United Kingdom .................... 9626512

[51] Int. Cl.⁷ .................................................. A61B 17/39
[52] U.S. Cl. ................................. 606/34; 606/32; 606/39
[58] Field of Search ............................. 606/32–35, 37–42

[56] References Cited

U.S. PATENT DOCUMENTS

| Re. 33,925 | 5/1992 | Bales et al. . |
|---|---|---|
| 164,184 | 6/1875 | Kidder . |
| 1,366,756 | 1/1921 | Wappler . |
| 1,735,271 | 11/1929 | Groff . |
| 1,814,791 | 7/1931 | Ende . |
| 1,889,609 | 11/1932 | Mutscheller . |
| 1,932,258 | 10/1933 | Wappler . |
| 1,943,543 | 1/1934 | McFadden . |
| 1,952,617 | 3/1934 | Wappler . |
| 1,983,669 | 12/1934 | Kimble . |
| 2,050,904 | 8/1936 | Trice . |

(List continued on next page.)

FOREIGN PATENT DOCUMENTS

| 0 013605 | 7/1980 | European Pat. Off. . |
|---|---|---|
| 0 049633 | 4/1982 | European Pat. Off. . |
| 0 067680 | 12/1982 | European Pat. Off. . |
| 0 136855 | 4/1985 | European Pat. Off. . |
| 0 219568 | 12/1985 | European Pat. Off. . |
| 0 205851 | 12/1986 | European Pat. Off. . |
| 0 280798A | 9/1988 | European Pat. Off. . |

(List continued on next page.)

OTHER PUBLICATIONS

Cook, Albert M. & John G. Webster, *Therapeutic Medical Devices Application and Design*, Prentice–Hall Inc., New Jersey, 1982, p. 349.

Pearce, John A., *Electrosurgery*, John Wiley & Sons Inc., New York, 1986, pp. 17, 69–75 and 87.

Wyeth, G.A., *Electrosurgical Unit*, pp. 1180–1202.

Everest Medical Technologies, Inc., "Everest Bipolar Laparoscopic Cholecystectomy," Transcript of Lecture by Dr. Olsen, Oct. 7, 1991.

(List continued on next page.)

*Primary Examiner*—Michael Peffley
*Attorney, Agent, or Firm*—Nixon & Vanderhye P.C.

[57] ABSTRACT

A radio frequency generator for an electrosurgical system is provided, the system including an electrode assembly having two electrodes for use immersed in an electrically conductive fluid. The generator has control circuitry for rapidly reducing the delivered radio frequency output power by at least 50% within at most a few cycles of the peak radio frequency output voltage reaching a predetermined threshold limit. In this way, tissue coagulation can be performed in, for example, saline without significant steam generation. The same peak voltage limitation technique is used in a tissue vaporisation or cutting mode to limit the size of the steam pocket at the electrodes and to avoid electrode burning. The generator has a push-pull output stage with a series-resonant output circuit, the output stage being driven by a radio frequency oscillator at a frequency which, in general, differs from the resonant frequency of the resonant output circuit. Power control is achieved by varying the ON-time of switching transistors forming the push-pull output pair and by altering the frequency spacing between the excitation frequency and the resonant frequency of the series-resonant output circuit. In an alternative embodiment, a bridge configuration using two push-pull pairs is used, yielding a further power control variable: the relative phase of the driving signals to the respective transistor pairs.

26 Claims, 5 Drawing Sheets

U.S. PATENT DOCUMENTS

| | | |
|---|---|---|
| 2,056,377 | 10/1936 | Wappler . |
| 2,196,171 | 4/1940 | Arnesen . |
| 2,888,928 | 6/1959 | Seiger . |
| 3,035,580 | 5/1962 | Guiorguiev . |
| 3,460,539 | 8/1969 | Anhalt, Sr. . |
| 3,595,239 | 7/1971 | Petersen . |
| 3,601,126 | 8/1971 | Estes . |
| 3,614,414 | 10/1971 | Gores . |
| 3,648,001 | 3/1972 | Anderson et al. . |
| 3,685,518 | 8/1972 | Beurle et al. . |
| 3,699,967 | 10/1972 | Anderson . |
| 3,707,149 | 12/1972 | Hao et al. . |
| 3,801,766 | 4/1974 | Morrison, Jr. . |
| 3,815,604 | 6/1974 | O'Malley . |
| 3,845,771 | 11/1974 | Vise . |
| 3,847,153 | 11/1974 | Weissman . |
| 3,870,047 | 3/1975 | Gonser . |
| 3,885,569 | 5/1975 | Judson . |
| 3,898,991 | 8/1975 | Ikuno et al. . |
| 3,901,242 | 8/1975 | Storz . |
| 3,902,494 | 9/1975 | Haberlen et al. . |
| 3,903,891 | 9/1975 | Brayshaw . |
| 3,920,021 | 11/1975 | Hiltebrandt . |
| 3,920,022 | 11/1975 | Pastor . |
| 3,923,063 | 12/1975 | Andrews et al. . |
| 3,929,137 | 12/1975 | Gonser et al. . |
| 3,939,839 | 2/1976 | Curtiss . |
| 3,945,375 | 3/1976 | Banko . |
| 3,963,030 | 6/1976 | Newton . |
| 3,964,487 | 6/1976 | Judson . |
| 3,970,088 | 7/1976 | Morrison . |
| 3,974,833 | 8/1976 | Durden, III . |
| 4,011,872 | 3/1977 | Komiya . |
| 4,016,881 | 4/1977 | Rioux et al. . |
| 4,024,467 | 5/1977 | Andrews et al. . |
| 4,033,351 | 7/1977 | Hetzel . |
| 4,040,426 | 8/1977 | Morrison, Jr. . |
| 4,043,342 | 8/1977 | Morrison, Jr. . |
| 4,051,855 | 10/1977 | Scheiderman . |
| 4,060,088 | 11/1977 | Morrison, Jr. et al. . |
| 4,069,827 | 1/1978 | Dominy . |
| 4,074,718 | 2/1978 | Morrison, Jr. . |
| 4,092,986 | 6/1978 | Schneiderman . |
| 4,114,623 | 9/1978 | Meinke et al. . |
| 4,116,198 | 9/1978 | Roos . |
| 4,119,102 | 10/1978 | LeVeen . |
| 4,126,137 | 11/1978 | Archibald . |
| 4,154,240 | 5/1979 | Ikuno et al. . |
| 4,189,685 | 2/1980 | Doss . |
| 4,200,104 | 4/1980 | Harris . |
| 4,202,337 | 5/1980 | Hren et al. . |
| 4,204,549 | 5/1980 | Paglione . |
| 4,210,152 | 7/1980 | Berry . |
| 4,228,800 | 10/1980 | Degler, Jr. et al. . |
| 4,248,231 | 2/1981 | Herczog et al. . |
| 4,271,837 | 6/1981 | Schuler . |
| 4,281,373 | 7/1981 | Mabille . |
| 4,301,802 | 11/1981 | Poler . |
| 4,326,529 | 4/1982 | Doss et al. . |
| 4,346,332 | 8/1982 | Walden . |
| 4,376,263 | 3/1983 | Pittroff et al. . |
| 4,381,007 | 4/1983 | Doss . |
| 4,416,277 | 11/1983 | Newton et al. . |
| 4,418,692 | 12/1983 | Guay . |
| 4,429,698 | 2/1984 | Bentall . |
| 4,448,198 | 5/1984 | Turner . |
| 4,474,179 | 10/1984 | Koch . |
| 4,476,862 | 10/1984 | Pao . |
| 4,492,231 | 1/1985 | Auth . |
| 4,494,541 | 1/1985 | Archibald . |
| 4,512,338 | 4/1985 | Balko et al. . |
| 4,517,976 | 5/1985 | Murakoshi et al. . |
| 4,524,770 | 6/1985 | Orandi . |
| 4,532,924 | 8/1985 | Auth et al. . |
| 4,534,347 | 8/1985 | Taylor . |
| 4,548,207 | 10/1985 | Reimels . |
| 4,559,943 | 12/1985 | Bowers . |
| 4,559,951 | 12/1985 | Dahl et al. . |
| 4,562,838 | 1/1986 | Walker . |
| 4,565,200 | 1/1986 | Cosman . |
| 4,567,890 | 2/1986 | Ohta et al. . |
| 4,580,557 | 4/1986 | Hertzmann . |
| 4,590,934 | 5/1986 | Malis et al. . |
| 4,593,691 | 6/1986 | Lindstrom et al. . |
| 4,617,927 | 10/1986 | Manes . |
| 4,657,015 | 4/1987 | Irnich . |
| 4,658,819 | 4/1987 | Harris . |
| 4,658,820 | 4/1987 | Klicek . |
| 4,669,468 | 6/1987 | Cartmell et al. . |
| 4,674,499 | 6/1987 | Pao . |
| 4,681,122 | 7/1987 | Winters et al. . |
| 4,682,596 | 7/1987 | Bales et al. . |
| 4,688,569 | 8/1987 | Rabinowitz . |
| 4,696,668 | 9/1987 | Wilcox . |
| 4,706,667 | 11/1987 | Roos . |
| 4,709,698 | 12/1987 | Johnston et al. . |
| 4,712,544 | 12/1987 | Ensslin . |
| 4,727,874 | 3/1988 | Bowers . |
| 4,735,201 | 4/1988 | O'Reilly . |
| 4,769,005 | 9/1988 | Ginsburg et al. . |
| 4,781,175 | 11/1988 | McGreevy et al. . |
| 4,799,480 | 1/1989 | Abraham et al. . |
| 4,800,899 | 1/1989 | Elliott . |
| 4,802,476 | 2/1989 | Noerenberg et al. . |
| 4,805,616 | 2/1989 | Pao . |
| 4,813,429 | 3/1989 | Eshel et al. . |
| 4,820,298 | 4/1989 | Leveen et al. . |
| 4,823,791 | 4/1989 | D'Amelio et al. . |
| 4,827,927 | 5/1989 | Newton . |
| 4,832,048 | 5/1989 | Cohen . |
| 4,850,353 | 7/1989 | Stasz et al. . |
| 4,860,744 | 8/1989 | Johnson et al. . |
| 4,878,493 | 11/1989 | Pasternak et al. . |
| 4,886,074 | 12/1989 | Bisping . |
| 4,919,129 | 4/1990 | Weber, Jr. et al. . |
| 4,920,978 | 5/1990 | Colvin . |
| 4,931,047 | 6/1990 | Broadwin et al. . |
| 4,936,281 | 6/1990 | Stasz . |
| 4,936,301 | 6/1990 | Rexroth et al. . |
| 4,936,310 | 6/1990 | Engstrom et al. . |
| 4,936,842 | 6/1990 | D'Amelio et al. . |
| 4,943,290 | 7/1990 | Rexroth et al. . |
| 4,950,267 | 8/1990 | Ishihara et al. . |
| 4,955,377 | 9/1990 | Lennox et al. . |
| 4,966,597 | 10/1990 | Cosman . |
| 4,967,765 | 11/1990 | Turner et al. . |
| 4,969,885 | 11/1990 | Farin . |
| 4,976,711 | 12/1990 | Parins et al. . |
| 4,994,069 | 2/1991 | Ritchart et al. . |
| 4,998,933 | 3/1991 | Eggers et al. . |
| 5,007,908 | 4/1991 | Rydell . |
| 5,009,656 | 4/1991 | Reimels . |
| 5,013,312 | 5/1991 | Parins et al. . |
| 5,019,076 | 5/1991 | Yamanashi et al. . |
| 5,035,696 | 7/1991 | Rydell . |
| 5,037,379 | 8/1991 | Clayman et al. . |
| 5,047,026 | 9/1991 | Rydell . |
| 5,047,027 | 9/1991 | Rydell . |
| 5,057,107 | 10/1991 | Parins et al. . |
| 5,062,031 | 10/1991 | Flachenecker . |
| 5,071,418 | 12/1991 | Rosenbaum . |
| 5,080,660 | 1/1992 | Buelna . |

6,093,186
Page 3

| | | |
|---|---|---|
| 5,083,565 | 1/1992 | Parins . |
| 5,085,659 | 2/1992 | Rydell . |
| 5,088,997 | 2/1992 | Delahuerga et al. . |
| 5,098,431 | 3/1992 | Rydell . |
| 5,099,840 | 3/1992 | Goble . |
| 5,108,391 | 4/1992 | Flachenecker . |
| 5,108,407 | 4/1992 | Geremia et al. . |
| 5,117,978 | 6/1992 | Blumenfeld et al. . |
| 5,122,138 | 6/1992 | Manwaring . |
| 5,133,365 | 7/1992 | Heil, Jr. et al. . |
| 5,158,561 | 10/1992 | Rydell et al. . |
| 5,167,658 | 12/1992 | Ensslin . |
| 5,167,659 | 12/1992 | Ohtomo et al. . |
| 5,171,255 | 12/1992 | Rydell . |
| 5,171,311 | 12/1992 | Rydell et al. . |
| 5,178,620 | 1/1993 | Eggers et al. . |
| 5,190,517 | 3/1993 | Zieve . |
| 5,195,959 | 3/1993 | Smith . |
| 5,196,007 | 3/1993 | Ellman et al. . |
| 5,197,963 | 3/1993 | Parins . |
| 5,201,743 | 4/1993 | Haber et al. . |
| 5,207,675 | 5/1993 | Canady . |
| 5,217,457 | 6/1993 | Delahuerga et al. . |
| 5,217,458 | 6/1993 | Parins . |
| 5,217,459 | 6/1993 | Kamerling . |
| 5,221,281 | 6/1993 | Klicek . |
| 5,244,462 | 9/1993 | Delahuerga et al. . |
| 5,249,585 | 10/1993 | Turner et al. . |
| 5,250,047 | 10/1993 | Rydell . |
| 5,258,006 | 11/1993 | Rydell et al. . |
| 5,259,395 | 11/1993 | Li . |
| 5,261,906 | 11/1993 | Pennino et al. . |
| 5,267,994 | 12/1993 | Gentelia et al. . |
| 5,267,997 | 12/1993 | Farin . |
| 5,277,201 | 1/1994 | Stern . |
| 5,277,696 | 1/1994 | Hagen . |
| 5,281,213 | 1/1994 | Milder et al. . |
| 5,281,216 | 1/1994 | Klicek . |
| 5,282,799 | 2/1994 | Rydell . |
| 5,282,845 | 2/1994 | Bush et al. . |
| 5,290,282 | 3/1994 | Casscells . |
| 5,290,283 | 3/1994 | Suda . |
| 5,300,068 | 4/1994 | Rosar . |
| 5,300,069 | 4/1994 | Hunsberger et al. . |
| 5,300,070 | 4/1994 | Gentelia et al. . |
| 5,304,214 | 4/1994 | DeFord et al. . |
| 5,306,238 | 4/1994 | Fleenor . |
| 5,317,155 | 5/1994 | King . |
| 5,318,563 | 6/1994 | Malis . |
| 5,320,627 | 6/1994 | Sorensen et al. . |
| 5,330,470 | 7/1994 | Hagen . |
| 5,330,471 | 7/1994 | Eggers . |
| 5,334,193 | 8/1994 | Nardella . |
| 5,334,198 | 8/1994 | Hart et al. . |
| 5,336,222 | 8/1994 | Durgin, Jr. et al. . |
| 5,342,357 | 8/1994 | Nardella . |
| 5,342,391 | 8/1994 | Foshee et al. . |
| 5,344,428 | 9/1994 | Griffiths . |
| 5,352,222 | 10/1994 | Rydell . |
| 5,354,296 | 10/1994 | Turkel . |
| 5,366,443 | 11/1994 | Eggers . |
| 5,370,645 | 12/1994 | Klicek et al. . |
| 5,370,675 | 12/1994 | Edwards et al. . |
| 5,372,596 | 12/1994 | Klicek et al. . |
| 5,382,247 | 1/1995 | Cimino et al. . |
| 5,383,874 | 1/1995 | Jackson et al. . |
| 5,383,876 | 1/1995 | Nardella . |
| 5,383,917 | 1/1995 | Desai et al. . |
| 5,383,923 | 1/1995 | Webster, Jr. . |
| 5,395,363 | 3/1995 | Billings et al. . |
| 5,395,368 | 3/1995 | Ellman et al. . |
| 5,403,311 | 4/1995 | Abele et al. . |
| 5,419,767 | 5/1995 | Eggers et al. . |
| 5,422,567 | 6/1995 | Matsuanga . |
| 5,422,808 | 6/1995 | Edwards . |
| 5,423,809 | 6/1995 | Klicek . |
| 5,423,810 | 6/1995 | Goble . |
| 5,423,811 | 6/1995 | Imran et al. . |
| 5,431,649 | 7/1995 | Mulier et al. . |
| 5,437,662 | 8/1995 | Nardella . |
| 5,438,302 | 8/1995 | Goble . |
| 5,441,499 | 8/1995 | Fritzsch . |
| 5,443,470 | 8/1995 | Stern et al. . |
| 5,454,809 | 10/1995 | Janssen . |
| 5,462,521 | 10/1995 | Brucker et al. . |
| 5,472,441 | 12/1995 | Edwards et al. . |
| 5,472,443 | 12/1995 | Cordis . |
| 5,480,397 | 1/1996 | Eggers et al. . |
| 5,480,398 | 1/1996 | Eggers et al. . |
| 5,496,312 | 3/1996 | Klicek . |
| 5,496,314 | 3/1996 | Eggers . |
| 5,505,728 | 4/1996 | Ellman et al. . |
| 5,505,730 | 4/1996 | Edwards . |
| 5,507,743 | 4/1996 | Edwards et al. . |
| 5,514,129 | 5/1996 | Smith . |
| 5,514,130 | 5/1996 | Baker . |
| 5,514,131 | 5/1996 | Edwards et al. . |
| 5,520,684 | 5/1996 | Imran . |
| 5,520,685 | 5/1996 | Wojciechowicz . |
| 5,522,815 | 6/1996 | Durgin, Jr. et al. . |
| 5,531,744 | 7/1996 | Nardella et al. . |
| 5,536,267 | 7/1996 | Edwards et al. . |
| 5,540,680 | 7/1996 | Guglielmi et al. . |
| 5,540,681 | 7/1996 | Strul et al. . |
| 5,540,682 | 7/1996 | Gardner et al. . |
| 5,540,683 | 7/1996 | Ichikawa et al. . |
| 5,540,684 | 7/1996 | Hassler, Jr. . |
| 5,540,685 | 7/1996 | Parins et al. . |
| 5,542,916 | 8/1996 | Hirsch et al. . |
| 5,542,945 | 8/1996 | Fritzsch . |
| 5,545,161 | 8/1996 | Imran . |
| 5,545,193 | 8/1996 | Fleischman et al. . |
| 5,549,605 | 8/1996 | Hahnen . |
| 5,554,172 | 9/1996 | Horner et al. . |
| 5,555,618 | 9/1996 | Winkler . |
| 5,556,396 | 9/1996 | Cohen et al. . |
| 5,556,397 | 9/1996 | Long et al. . |
| 5,558,671 | 9/1996 | Yates . |
| 5,562,720 | 10/1996 | Stern et al. . |
| 5,569,164 | 10/1996 | Lurz . |
| 5,569,242 | 10/1996 | Lax et al. . |
| 5,569,244 | 10/1996 | Hahnen . |
| 5,569,245 | 10/1996 | Guglielmi et al. . |
| 5,571,100 | 11/1996 | Goble et al. . |
| 5,575,789 | 11/1996 | Bell et al. . |
| 5,578,007 | 11/1996 | Imran . |
| 5,582,609 | 12/1996 | Swanson et al. . |
| 5,582,610 | 12/1996 | Grossi et al. . |
| 5,584,830 | 12/1996 | Ladd et al. . |
| 5,591,141 | 1/1997 | Nettekoven . |
| 5,599,344 | 2/1997 | Paterson . |
| 5,599,345 | 2/1997 | Edwards et al. . |
| 5,599,346 | 2/1997 | Edwards et al. . |
| 5,599,347 | 2/1997 | Hart et al. . |
| 5,599,348 | 2/1997 | Gentelia et al. . |
| 5,599,349 | 2/1997 | D'Amelio . |
| 5,603,711 | 2/1997 | Parins et al. . |
| 5,603,712 | 2/1997 | Koranda et al. . |
| 5,607,422 | 3/1997 | Smeets et al. . |
| 5,609,151 | 3/1997 | Mulier et al. . |
| 5,609,573 | 3/1997 | Sandock . |
| 5,611,798 | 3/1997 | Eggers . |
| 5,620,481 | 4/1997 | Desai et al. . |
| 5,624,439 | 4/1997 | Edwards et al. . |

| | | | | | |
|---|---|---|---|---|---|
| 5,626,560 | 5/1997 | Soring . | 222207 | 5/1985 | German Dem. Rep. . |
| 5,626,575 | 5/1997 | Crenner . | 651428 | 9/1937 | Germany . |
| 5,626,576 | 5/1997 | Janssen . | 1007960 | 5/1957 | Germany . |
| 5,626,578 | 5/1997 | Tihon . | 2222820 | 11/1973 | Germany . |
| 5,628,745 | 5/1997 | Bek . | 2457900 | 5/1976 | Germany . |
| 5,628,771 | 5/1997 | Mizukawa et al. . | 2930982 | 2/1981 | Germany . |
| 5,630,426 | 5/1997 | Eggers et al. . | 3209444 | 10/1982 | Germany . |
| 5,633,578 | 5/1997 | Eggers et al. . | 3215832A | 11/1982 | Germany . |
| 5,634,924 | 6/1997 | Turkel et al. . | 3119735 | 1/1983 | Germany . |
| 5,647,869 | 7/1997 | Goble et al. . | 3245570 | 6/1984 | Germany . |
| 5,672,174 | 9/1997 | Gough et al. . | 3423356 | 1/1986 | Germany . |
| 5,683,366 | 11/1997 | Eggers et al. . | 3427517 | 1/1986 | Germany . |
| 5,693,045 | 12/1997 | Eggers . | 3511107 | 10/1986 | Germany . |
| 5,697,281 | 12/1997 | Eggers et al. . | 3623688 | 1/1987 | Germany . |
| 5,697,536 | 12/1997 | Eggers et al. . | 3530335 | 3/1987 | Germany . |
| 5,697,882 | 12/1997 | Eggers et al. . | 3707820 | 9/1987 | Germany . |
| 5,697,909 | 12/1997 | Eggers et al. . | 3622337 C2 | 1/1988 | Germany . |
| 5,700,262 | 12/1997 | Acosta et al. . | 3642077 C2 | 6/1988 | Germany . |
| 5,725,524 | 3/1998 | Mulier et al. . | 3708801 C2 | 9/1988 | Germany . |
| 5,766,153 | 6/1998 | Eggers et al. . | 3824913 | 2/1990 | Germany . |
| 5,810,764 | 9/1998 | Eggers et al. . | 3838840 C2 | 5/1990 | Germany . |
| 5,833,689 | 11/1998 | Long . | 3930451 | 3/1991 | Germany . |
| 5,843,019 | 12/1998 | Eggers et al. . | 4108269 C2 | 6/1992 | Germany . |
| 5,860,951 | 1/1999 | Eggers et al. . | 4103972 C2 | 8/1992 | Germany . |
| 5,871,469 | 2/1999 | Eggers et al. . | 4126608 | 2/1993 | Germany . |
| 5,873,855 | 2/1999 | Eggers et al. . | 4139029 C2 | 6/1993 | Germany . |
| 5,888,198 | 3/1999 | Eggers et al. . | 4217999 A1 | 12/1993 | Germany . |
| 5,891,095 | 4/1999 | Eggers et al. . | 4237321 A1 | 5/1994 | Germany . |
| 5,902,272 | 5/1999 | Eggers et al. . | 4323585 | 1/1995 | Germany . |
| | | | 4339049 | 5/1995 | Germany . |

FOREIGN PATENT DOCUMENTS

| | | | | | |
|---|---|---|---|---|---|
| | | | 4425015 | 1/1996 | Germany . |
| 0 310431 | 4/1989 | European Pat. Off. . | 195 30 004 | 3/1996 | Germany . |
| 0 316469 | 5/1989 | European Pat. Off. . | 4429478 | 3/1996 | Germany . |
| 0 325456 | 7/1989 | European Pat. Off. . | 195 10 185 | 10/1996 | Germany . |
| 0 332308 | 9/1989 | European Pat. Off. . | 195 12 640 C2 | 10/1996 | Germany . |
| 0 373670 | 6/1990 | European Pat. Off. . | 195 14 552 | 10/1996 | Germany . |
| 0 392837 | 10/1990 | European Pat. Off. . | 195 14 553 C1 | 10/1996 | Germany . |
| 0 407057 | 1/1991 | European Pat. Off. . | 195 26 243 C1 | 1/1997 | Germany . |
| 0 412426 | 2/1991 | European Pat. Off. . | 195 26 244 | 1/1997 | Germany . |
| 0 437377 | 7/1991 | European Pat. Off. . | 195 43 547 C1 | 1/1997 | Germany . |
| 0 448798 | 10/1991 | European Pat. Off. . | 196 30 601 | 2/1997 | Germany . |
| 0 499491 | 8/1992 | European Pat. Off. . | 195 37 897 | 3/1997 | Germany . |
| 0 507622 | 10/1992 | European Pat. Off. . | 195 42 417 | 5/1997 | Germany . |
| 0 509670 | 10/1992 | European Pat. Off. . | 195 42 418 | 5/1997 | Germany . |
| 0 517243 | 12/1992 | European Pat. Off. . | 195 42 419 | 5/1997 | Germany . |
| 0 518230 | 12/1992 | European Pat. Off. . | 195 45 539 | 6/1997 | Germany . |
| 0 530400 | 3/1993 | European Pat. Off. . | 195 45 756 | 6/1997 | Germany . |
| 0 536440 | 4/1993 | European Pat. Off. . | 196 50 797 | 6/1997 | Germany . |
| 0 558316 | 9/1993 | European Pat. Off. . | 62-211060 | 9/1987 | Japan . |
| 0 558318 | 9/1993 | European Pat. Off. . | 243478 | 7/1946 | Switzerland . |
| 0 647435 | 4/1995 | European Pat. Off. . | 644491 | 1/1979 | U.S.S.R. . |
| 0 653192 | 5/1995 | European Pat. Off. . | 2 164 473 | of 1876 | United Kingdom . |
| 0 674909 | 10/1995 | European Pat. Off. . | 1361497 | 7/1974 | United Kingdom . |
| 0 684015 | 11/1995 | European Pat. Off. . | 2037167 | 7/1980 | United Kingdom . |
| 0 688536 | 12/1995 | European Pat. Off. . | 1583397 | 1/1981 | United Kingdom . |
| 0 692224 | 1/1996 | European Pat. Off. . | 2133290 | 7/1984 | United Kingdom . |
| 0 694290 | 1/1996 | European Pat. Off. . | 2145932 | 4/1985 | United Kingdom . |
| 0 697199 | 2/1996 | European Pat. Off. . | 2161081 | 1/1986 | United Kingdom . |
| 0 709065 | 5/1996 | European Pat. Off. . | 2177309 | 1/1987 | United Kingdom . |
| 0 714635 | 6/1996 | European Pat. Off. . | 2179861 | 3/1987 | United Kingdom . |
| 0 717967 | 6/1996 | European Pat. Off. . | 2213381 | 8/1989 | United Kingdom . |
| 0 732080 | 9/1996 | European Pat. Off. . | 2214430 | 9/1989 | United Kingdom . |
| 0 733345 | 9/1996 | European Pat. Off. . | WO 81/03271 | 11/1981 | WIPO . |
| 0 737447 | 10/1996 | European Pat. Off. . | WO 82/00084 | 1/1982 | WIPO . |
| 0 740926 | 11/1996 | European Pat. Off. . | WO 82/02488 | 8/1982 | WIPO . |
| 0754437 | 1/1997 | European Pat. Off. . | WO 84/03829 | 10/1984 | WIPO . |
| 57862 | 9/1953 | France . | WO 88/01851 | 3/1988 | WIPO . |
| 1215305 | 4/1960 | France . | WO 90/03152 | 4/1990 | WIPO . |
| 1454773 | 10/1966 | France . | | | |
| 2313949 | 1/1977 | France . | | | |
| 2443829 | 7/1980 | France . | | | |
| 2501034 | 9/1982 | France . | | | |

| | | |
|---|---|---|
| WO 93/08756 | 5/1993 | WIPO . |
| WO 93/13718 | 7/1993 | WIPO . |
| WO 93/13816 | 7/1993 | WIPO . |
| WO 93/16650 | 9/1993 | WIPO . |
| WO 93/19681 | 10/1993 | WIPO . |
| WO 93/19682 | 10/1993 | WIPO . |
| WO 93/20747 | 10/1993 | WIPO . |
| WO 93/20877 | 10/1993 | WIPO . |
| WO 94/04220 | 3/1994 | WIPO . |
| WO 94/06510 | 3/1994 | WIPO . |
| WO 94/10921 | 5/1994 | WIPO . |
| WO 94/10924 | 5/1994 | WIPO . |
| WO 94/10925 | 5/1994 | WIPO . |
| WO 94/23659 | 10/1994 | WIPO . |
| WO 94/26228 | 11/1994 | WIPO . |
| WO 94/28809 | 12/1994 | WIPO . |
| WO 95/02369 | 1/1995 | WIPO . |
| WO 95/05781 | 3/1995 | WIPO . |
| WO 95/09576 | 4/1995 | WIPO . |
| WO 95/09577 | 4/1995 | WIPO . |
| WO 95/10320 | 4/1995 | WIPO . |
| WO 95/10321 | 4/1995 | WIPO . |
| WO 95/17855 | 7/1995 | WIPO . |
| WO 95/18575 | 7/1995 | WIPO . |
| WO 95/19733 | 7/1995 | WIPO . |
| WO 95/20360 | 8/1995 | WIPO . |
| WO 95/23558 | 9/1995 | WIPO . |
| WO 95/24160 | 9/1995 | WIPO . |
| WO 95/25472 | 9/1995 | WIPO . |
| WO 95/26686 | 10/1995 | WIPO . |
| WO 95/30377 | 11/1995 | WIPO . |
| WO 95/31144 | 11/1995 | WIPO . |
| WO 96/00036 | 1/1996 | WIPO . |
| WO 96/00039 | 1/1996 | WIPO . |
| WO 96/00040 | 1/1996 | WIPO . |
| WO 96/00042 | 1/1996 | WIPO . |
| WO 96/00043 | 1/1996 | WIPO . |
| WO 96/00528 | 1/1996 | WIPO . |
| WO 96/04859 | 2/1996 | WIPO . |
| WO 96/07360 | 3/1996 | WIPO . |
| WO 96/09010 | 3/1996 | WIPO . |
| WO 96/10367 | 4/1996 | WIPO . |
| WO 96/14020 | 5/1996 | WIPO . |
| WO 96/14021 | 5/1996 | WIPO . |
| WO 96/18349 | 6/1996 | WIPO . |
| WO 96/19152 | 6/1996 | WIPO . |
| WO 96/23448 | 8/1996 | WIPO . |
| WO 96/23449 | 8/1996 | WIPO . |
| WO 96/24296 | 8/1996 | WIPO . |
| WO 96/24301 | 8/1996 | WIPO . |
| WO 96/27337 | 9/1996 | WIPO . |
| WO 96/29946 | 10/1996 | WIPO . |
| WO 96/32897 | 10/1996 | WIPO . |
| WO 96/34567 | 11/1996 | WIPO . |
| WO 96/34569 | 11/1996 | WIPO . |
| WO 96/34570 | 11/1996 | WIPO . |
| WO 96/34571 | 11/1996 | WIPO . |
| WO 96/37146 | 11/1996 | WIPO . |
| WO 96/38094 | 12/1996 | WIPO . |
| WO 96/39085 | 12/1996 | WIPO . |
| WO 96/39086 | 12/1996 | WIPO . |
| WO 96/39088 | 12/1996 | WIPO . |
| WO 96/39089 | 12/1996 | WIPO . |
| WO 96/39966 | 12/1996 | WIPO . |
| WO 96/39967 | 12/1996 | WIPO . |
| WO 97/00646 | 1/1997 | WIPO . |
| WO 97/00647 | 1/1997 | WIPO . |
| PCT/GB97/ 00066 | 5/1997 | WIPO . |

OTHER PUBLICATIONS

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

Schurr, M. O. et al., "Histologic Effects of Different Technologies for Dissection in Endoscopic Surgery:Nd:YAG Laser, High Frequency and Water–Jet," End. Surg., vol. 2, 1994, pp. 195–201.

Newman, Laura, "Could Twist on TURP Knock Lasers Out," Urology Times, vol. 3, No. 3, Mar. 1995, p. 21.

ArthroCare Corporation, "The Arthrocare Arthroscopic System," 1995.

Tucker, R.D. et al., "In Vivo Effect of 5 French Bipolar and Monopolar Electro–Surgical Probes on Porcine Bladder," Urological Research, Springer–Verlag 1990, 18:291–294.

Kramolowsky, Eugene V. et al., "The Urological Application of Electrosurgery," The Journal of Urology, vol. 146, Sep. 1991, pp. 669–674.

Tucker, Robert D. et al., "A Comparison of Urologic Application of Bipolar Versus Monopolar Five French Electrosurgical Probes," The Journal of Urology, vol. 141, Mar. 1989, pp. 662–665.

Kramolowsky, Eugene V. et al., "Use of 5F Bipolar Electrosurgical Probe in Endoscopic Urological Procedures," The Journal of Urology, vol. 143, Feb. 1990, pp. 275–277.

Tucker, Robert et al., "A Bipolar Electrosurgical TURP Loop," Abstract of Paper P14–11, $7^{th}$ World Congress on Endourology and ESWL, Nov. 27–30, Kyoto, Japan, 1989, p. 248.

Ramsay, J.W. A. et a., "A Comparison of Bipolar and Monopolar Diathermy Probes in Experimental Animals," Urological Research, Springer–Verlag 1985, 13:99–102.

German Article w/ Translation: Elsasser, E. and Roos, E., "Concerning an Instrument for Transurethral Resection without Leakage of Current," Medizinal–Marks/Acta Medicotechnica, vol. 24, No. 4, 1976, pp. 129–134.

Nardella, Paul C., "Radio Frequency Energy and Impedance Feedback," SPIE, vol. 1068, Catheter–Based Sensing & Imaging Technology, 1989, pp. 42–48.

Honig, William M., "The Mechanism of Cutting in Electrosurgery," IEEE Transactions on Biomedical Engineering, Jan. 1975, pp. 58–65.

Barry, Kevin J. et al., "The Effect of Radiofrequency–Generated Thermal Energy on the Mechanical and Histologic Characteristics of the Arterial Wall In Vivo: Implications for Radiofrequency Angioplasty," American Heart Journal, vol. 117, No. 2, Feb. 1989, pp. 332–341.

Slager, Cornelis J. et al., "Vaporization of Atherosclerotic Plaques by Spark Erosion," Journal of American College of Cardiology, 1985, pp. 1382–6.

Lee, Benjamin I. et al., "Thermal Compression and Molding of Atherosclerotic Vascular Tissue with Use of Radiofrequency Energy: Implications for Radiofrequency Balloon Angioplasty," Journal of American College of Cardiology, vol. 13, No. 5, Apr. 1989, pp. 1167–1175.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulation: Bipolar vs. Monopolar in the Treatment of Experimental Canine Gastric Ulcer Bleeding," Gastroenterology, vol. 80, No. 3, 1981, pp. 451–455.

Johnston, James H. et al., "Experimental Comparison of Endoscopic Yttrium–Aluminum–Garnet Laser, Electrosurgery, and Heater Probe for Canine Gut Arterial Coagulation," Gastroenterology, vol. 92, No. 5, May 1987, pp. 1101–1108.

Dennis, M.B. et al., "Evaluation of Electrofulguration in Control of Bleeding of Experimental Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Sciences, vol. 26, No. 7, Jul. Supplement 1981, pp. 31s–40s.

Auth, D.C., "Animal Testing of Endoscopic Hemostasis with Lasers and Other Devices," Endoscopy, vol. 18, Supplement 2, May 1986, pp. 36–39.

McLean, A. J., "The Bovie Electrosurgical Current Generator—Some Underlying Principles and Results," Archives of Surgery, vol. 18, 1929, pp. 1863–1873.

McLean, A. J., "Characteristics of Adequate Electrosurgical Current," American Journal of Surgery, vol. XVIII, No. 3, Feb. 16, 1932, pp. 417–441.

Wattiez, Arnaud et al., *Electrosurgery in Operative Endoscopy*, Blackwell Science Ltd., London, 1995, pp. 87–93, 155–163.

Farin, G., "Pneumatically Controlled Bipolar Cutting Instrument," End. Surg., 1993, pp. 1–3.

Muller, W., "The Advantages of Laparoscopic Assisted Bipolar High–Frequency Surgery," End. Surg., 1993, pp. 1–6.

Reidenbach, H. D., "Fundamentals of Bipolar High–Frequency Surgery," End. Surg. 1993, pp. 85–90.

Penketh, Richard et al., "Clinical Evaluation of the Procision Bipolar Electrosurgical Generator During Laparoscopic Gynaecological Procedures," EAES, $2^{nd}$ International Congress of the European Association for Endoscopic Surgery, Madrid, Sep. 15–17, 1994.

Lloyd, David M. et al., "A New Portable Bipolar Generator–Use in Laparoscopic Cholecystectomy," EAES, $2^{nd}$ International Congress of the European Association for Endoscopic Surgery, Madrid, Sep. 15–17, 1994.

Buchelt, Martin et al., "Excimer Laser Ablation of Fibrocartilage: An In Vitro and In Vivo Study," Lasers in Surgery and Medicine, vol. 11, 1991, pp. 271–279.

Srinivasan, R., "Ablation of Polymers and Biological Tissue by Ultraviolet Lasers," Science, vol. 234, Oct. 31, 1986, pp. 559–565.

Pearce, John A., "Chapter 3 Electrosurgery," *Handbook of Biomedical Engineering*, Ed. Jacob Kline, Academic Press, Inc., 1988, pp. 99–113.

Selikowitz, Stuart M. et al., "Electric Current and Voltage Recordings on the Myocardium During Electrosurgical Procedures in Canines," Reprint from *Surgery, Gynecology & Obstetrics*, Mar. 1987, vol. 164, pp. 219–224.

Tucker, Robert D. et al., "Demodulated Low Frequency Currents from Electrosurgical Procedures," Surgery, Gynecology & Obstetrics, Jul. 1984, vol. 159, pp. 39–43.

Lu, David Y. et al., "Electrical Thermal Angioplasty: Catheter Design Features, In Vitro Tissue Ablation Studies and In Vivo Experimental Findings," Am J Cardiol, vol. 60, 1987, pp. 1117–1122.

Malis, Leonard I., "Electrosurgery: Technical Note," J. Neurosurg., vol. 85, 1996, pp. 970–975.

Slager, C. J. et al., "Spark Erosion of Arteriosclerotic Plaques," Kardiologie, vol. 76, Suppl. 6, 1987, pp. 67–71.

Geddes, Leslie A., *Medical Device Accidents—With Illustrative Cases*, CRC Press, New York, 1998, p. 93 (commentary on Honig, William M., "The Mechanism of Cutting in Electrosurgery," IEEE Transactions on Biomedical Engineering, Jan. 1975, pp. 58–65).

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparoscopic Surgery," Advances in Bipolar Electrosurgery, pp. 1–4.

Description of Codman and Johnson & Johnson Malis CMC–III Bipolar System.

Pfizer/Valleylab Press Release "Valleylab Inc. Introduces The Procision Bipolar Electrosurgery System," Sep. 15, 1994.

ArthroCare Corporation, "ArthroCare Arthroscopic Electrosurgery System, Model 970 Operator's Manual," Feb. 1996.

ELECTROSURGICAL GENERATOR AND SYSTEM

FIELD OF THE INVENTION

This invention relates to an electrosurgical generator for delivering electrosurgical energy particularly but not exclusively in so-called underwater electrosurgery. The invention also relates to an electrosurgical system comprising the combination of a generator and an electrode assembly.

The term "underwater electrosurgery" is used in this specification to denote surgery performed using an electrosurgical instrument with a treatment electrode or electrodes immersed in liquid at the operation site, generally liquid introduced to distend a body cavity containing the operation site or to wash blood away from the site. Alternatively, surgery may be performed with the electrode or electrodes immersed in naturally occurring body fluids. The invention has particular application in the fields of urology, hysteroscopy and arthroscopy. It should be understood, however, that the invention includes features which may have application also in electrosurgery not involving electrode immersion.

BACKGROUND OF THE INVENTION

The background to underwater electrosurgery and intra-cavitary surgery, i.e. surgery in which living tissue is treated by least invasive surgical access to a body cavity, is described in our co-pending European Patent Application No. 96304558.8 (0754437), the contents of which are incorporated in this specification by reference.

Effective electrosurgical treatment of tissue which is totally immersed in liquid at the application site is difficult to achieve because the heat generated by the flow of electrical currents in both the tissue being treated and surrounding conductive liquid tends to cause boiling of the liquid. The operating electrode is intermittently surrounded by water vapour rather than liquid, with consequent large variations in the electrical impedance of the load presented to the generator supplying the electrosurgical power to the electrode. Whilst this variation is mitigated by use of a non-conductive liquid, it cannot be eliminated entirely due to the release of body fluids at the operative site which elevates the electrical conductance of the liquid. Changes in tissue type also alter the load impedance. These effects result in difficulty in controlling the electrosurgical output to produce consistent effects on the tissue being treated. As a result, high powers are commonly employed to overcome this performance variation.

SUMMARY OF THE INVENTION

According to a first aspect of this invention, an electrosurgical generator for supplying radio frequency power to an electrical instrument comprises a radio frequency output stage having at least a pair of electrosurgical output lines for the delivery of radio frequency power to the instrument, a power supply coupled to the output stage for supplying power to the output stage, and control circuitry including sensing means for deriving a sensing signal representative of the radio frequency peak output voltage developed across the output lines, wherein the output stage comprises a series-resonant output circuit coupled to the output lines and a switching means coupled to the resonant output circuit, and wherein the control circuitry is operable to vary the switching intervals of the switching device to reduce the delivered radio frequency power in response to a predetermined condition of the sensing signal. In a preferred embodiment of the invention, the series-resonant output circuit comprises the series combination of an inductance and a capacitance, and is coupled to the switching means such that a switched radio frequency output waveform is developed across the series combination, the output lines of the generator being coupled to the series-resonant circuit to receive the radio frequency voltage developed across the inductance or the capacitance, preferably the inductance. The series combination may be coupled between the switching means and a ground connection or one of a pair of supply rails of the power supply means, one of the output lines of the generator being coupled to a junction between the inductance and the capacitance, and the other being preferably connected to the said ground connection or one of the said supply rails. With the capacitance connected to the switching means and the inductance connected to the ground connection or supply rail, the output line is preferably connected to the junction of the inductance and capacitance by a coupling capacitance which is of smaller value than the capacitance of the series resonant combination. Alternatively, the switching means may comprise semiconductor switches connected in a bridge configuration, the series combination being coupled between oppositely phased nodes of the switching means.

In order to achieve rapid power reduction when, for example, liquid in the region of electrodes connected to the generator vaporises, the switching means and control circuitry are so arranged that the on-time of the switching means can be reduced to the extent of causing at least a 50% reduction in delivered output power within 100 µs of a predetermined radio frequency peak output voltage threshold having been reached. (The term "peak output voltage" in this context includes voltages measured on a peak-to-peak basis). In other words, the generator is responsive to a sensing signal representing peak or peak-to-peak output voltage levels. The switching means may comprise a pair of electronic switches connected in a push-pull series arrangement between the power supply rails, with the series-resonant output circuit coupled to the connection between the electronic switches. Thus, to reduce the output power, the on-time of each switch, which is typically a power MOSFET, is reduced during respective radio frequency half cycles to cause the required power reduction.

By causing a control overshoot in the sense of reducing the output power by a greater amount than the increase needed to produce vaporisation, vapour bubbles are allowed to collapse. This allows surgery to be performed in a conductive fluid field, in particular in a saline solution. Large and rapid changes in load impedance can occur substantially without causing unwanted electrosurgical effects. For example, when it is desired to produce electrosurgical desiccation, any increase in impedance due to vaporisation of surrounding saline in the region of an electrode of the instrument which might otherwise lead to unwanted arcing at the required power level for effective desiccation can be largely prevented. When electrosurgical tissue cutting or tissue vaporisation is required, output voltage limitation can be used to prevent electrode burning and/or excessive tissue vaporisation.

To avoid overloading of semiconductor power devices used in the switching means, the switching means are preferably driven by an oscillator operating at a frequency different from the resonant frequency of the series-resonant output circuit. By operating the oscillator at an excitation frequency higher than the resonant frequency of the series resonant output circuit, the available power at comparatively high impedances associated with cutting or vaporisation can be increased, while operating the oscillator so as to excite the resonant circuit at a frequency lower than its resonant frequency is more suited to electrosurgical desiccation which involves comparatively low load impedances.

The control circuitry referred to above is preferably arranged such that at least a 50% reduction in output power is brought about in a period of less than 20 µs after the output voltage reaches the predetermined sensing signal threshold by reducing the period of conduction of the electronic switches during individual cycles of the radio frequency output signal. Such alteration in the period of conduction is advantageously achieved independently of any variation in supply voltage. In practice, the reduction in output power is brought about using a single control variable, i.e. the peak output voltage or peak-to-peak output voltage independently of supply voltage and independently of the delivered output power which, of course, varies according to load impedance and supply voltage. Thus, triggering of a power reduction occurs at the same preset output voltage threshold but at different output power and load impedance values, according to circumstances.

The technique of directly controlling the radio frequency output stage can be performed by repeatedly producing, firstly, a rapid reduction in the cycle-by-cycle conduction period of the power device from a peak level to a trough level when the output threshold is reached, followed by, secondly, a progressive increase in the conduction period until the conduction period again reaches its peak level, the radio frequency output voltage being monitored during the progressive increase.

The output stage preferably includes an output resonant circuit having a Q which is sufficiently high to remove switching noise from the switching device or devices of the stage without unduly slowing the response to the output voltage reaching the predetermined threshold. Typically, the Q is at least 1 and is also sufficient to achieve a crest factor below 1.5, the crest factor being the ratio of the peak and r.m.s. values of the output voltage waveform.

Other aspects of the invention include a generator for underwater electrosurgery having an output impedance in the range of from 100 ohms to 250 ohms, and preferably between 130 and 190 ohms. Such a generator has its radio frequency output stage operable to produce a CW (continuous wave) output, i.e. with a 100% duty cycle or without on/off pulse width modulation at a frequency lower than the r.f. oscillation frequency. In effect, the output stage may operate as an open loop stage.

According to a second aspect of the invention, there is provided an electrosurgical system including a generator for generating radio frequency power and an electrosurgical instrument having at least one electrode for use immersed in a conductive liquid, wherein the generator comprises an output stage including at least one radio frequency power device, a series-resonant output circuit, and at least a pair of output connections arranged to receive radio frequency power from the power device, one of the pair of connections being connected to the said electrode, and wherein the generator further comprises a control stage operable to reduce the conduction time of the power device during individual radio frequency cycles in response to a sensing signal representative of the voltage presented to the generator across the output connections exceeding a predetermined sensing signal threshold value, whereby the radio frequency power delivered to the electrode structure is rapidly reduced when the conductive liquid is vaporised. The electrode structure may include a distal treatment electrode and a liquid contact electrode spaced proximally from the distal electrode, both electrodes being for use surrounded by the conductive liquid and each being connected to a respective one of the pair of output connections the control stage being operable to reduce the reduction time of the power device when the conductive liquid at the distal electrode is vaporised. The electrosurgical instrument may provide an electrode structure having juxtaposed first and second electrodes for immersion in the conductive liquid, the first and second electrodes respectively forming a tissue contact electrode at an extreme distal end of the instrument and a return electrode proximally spaced from the tissue contact electrode.

The system may be switchable between at least a tissue desiccation mode and a tissue cutting or vaporisation mode using a mode selection control. In this case the control stage is operable automatically to adjust the radio frequency power suppled to the electrode structure to limit the peak generator output voltage to a first value when the desiccation mode is selected and to at least one second value when the cutting or vaporisation mode is selected, the second value or values being higher than the first value. The first and second values are advantageously in the ranges of from 150V to 200V, and from 250V to 600V respectively, these voltages being peak voltages.

The mode selection control may be coupled to the generator oscillator driving the power device so that, in the tissue desiccation mode, the oscillation frequency of the oscillator is lower than the resonant frequency of the series-resonant output circuit, yet in the tissue cutting or vaporisation mode is higher than that resonant frequency for improved output power at comparatively low and comparatively high impedances respectively, as mentioned above.

According to a third aspect of the invention, there is provided an electrosurgical generator for supplying radio frequency power to an electrosurgical instrument, the generator comprising a radio frequency output stage having at least a pair of electrosurgical output connections for the delivery of radio frequency power to the instrument, a radio frequency oscillator for feeding a radio frequency signal to the output stage, and control circuitry including sensing means for deriving a sensing signal representative of the radio frequency signal delivered from the output connections, wherein the output stage comprises a series-resonant output circuit coupled to the output connections, the resonant frequency of the series-resonant output circuit being different from the operation frequency of the oscillator, and wherein the control circuitry provides a feedback signal for controlling the delivered radio frequency power.

The invention will now be described in more detail below by way of example and with reference to the drawings.

DETAILED DESCRIPTION OF THE PREFERRED EMBODIMENTS

The preferred embodiment of the present invention is intended to form bipolar electrosurgery with electrodes immersed in a conductive liquid medium such as normal saline. Electrosurgery is performed using a system comprising a generator and an instrument, the instrument having a dual-electrode structure with the saline acting as a conductor between the tissue being treated and one of the electrodes, hereinafter called the "return electrode". The other electrode is applied directly to the tissue. This other electrode is hereinafter called the "active electrode".

Figures 1, 2:
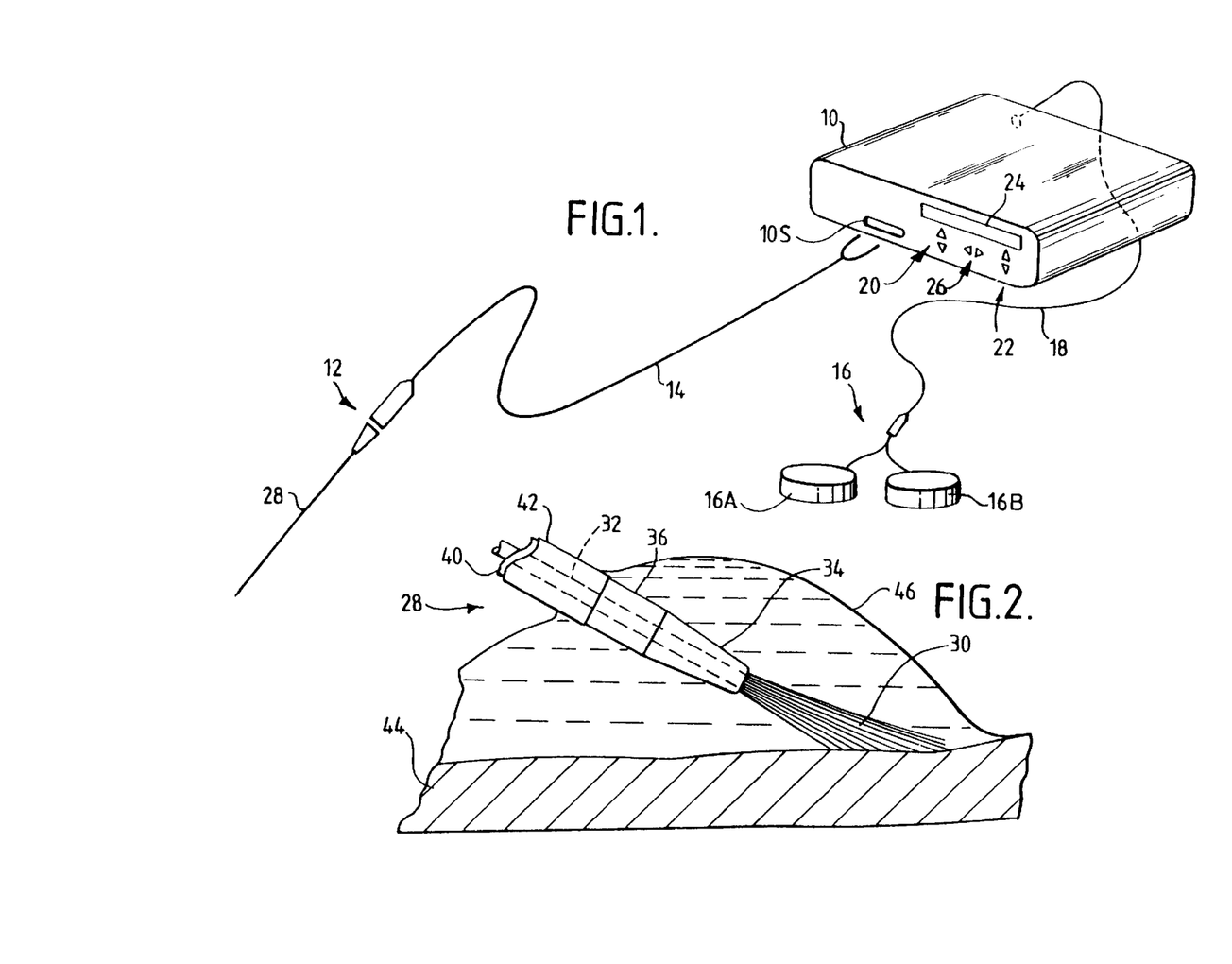
FIG. 1 is a diagram showing an electrosurgical system in accordance with the invention.
FIG. 2 is a fragmentary view of a first electrode assembly for tissue desiccation, shown in use and immersed in a conductive liquid.

Such a system is shown in FIG. 1. The generator 10 has an output socket 10S providing a radio frequency (RF) output for an instrument in the form of a handpiece 12 via a connection cord 14. Activation of the generator may be performed from the handpiece 12 via a control connection in cord 14 or by means of a footswitch unit 16, as shown, connected separately to the rear of the generator 10 by a footswitch connection cord 18. In the illustrated embodiment, footswitch unit 16 has two footswitches 16A and 16B for selecting a desiccation mode and a vaporisation mode of the generator respectively. The generator front panel has push buttons 20 and 22 for respectively setting desiccation and vaporisation power levels, which are indicated in a display 24. Push buttons 26 are provided as an alternative means for selection between desiccation and vaporisation modes.

Handpiece 12 mounts a detachable electrode assembly 28 having a dual electrode structure, as shown in the fragmentary view of FIG. 2.

FIG. 2 is an enlarged view of the distal end of electrode assembly 28. At its extreme distal end the assembly has an active electrode 30 which, in this embodiment, is formed as a series of metal filaments connected to a central conductor 32. The filaments may be made of stainless steel. Proximally of the active electrode 30 and spaced from the latter by a longitudinally and radially extending insulator 34 is a return electrode 36. The return electrode 36 is arranged coaxially around the inner conductor 32 as a sleeve 38 which extends as a tubular shaft 40 to the proximal end of the assembly 28 where it is connected in the handpiece 12 to conductors in the connection cord 14. Similarly, the inner conductor 32 extends to the handpiece and is connected to a conductor in cord 14. The electrode assembly 28 has an insulating sheath 42 which covers shaft 40 and terminates proximally of the insulator 34 to leave the distal end of shaft 40 exposed as the return electrode 36.

In operation as a desiccation instrument, the electrode assembly 28 is applied as shown in FIG. 2 to the tissue 44 to be treated, the operation site being immersed in a normal saline (0.9%w/v) solution, here shown as a drop 46 of liquid surrounding the distal end portion of the electrode assembly 28. The liquid immerses both the active electrode 30 and the return electrode 36.

Still referring again to FIG. 2, the metallic filaments forming the active electrode 30 are all electrically connected together and to the inner conductor 32 of the electrode assembly to form a unitary active electrode. Insulator 34 is an insulating sleeve, the distal end portion of which is exposed proximally of the exposed part of the active electrode 30. Typically, this sleeve is made of a ceramic material to resist damage from arcing. The return electrode terminates at a point short of the end of the insulator 36 so that it is both radially and axially spaced from the active, or tissue contact, electrode 30. The surface area of the return electrode is considerably greater than that of the active electrode 30. At the distal end of the electrode assembly, the diameter of the return electrode is typically in the region of from 1 mm to 3 mm, with the longitudinal extent of the exposed part of the return electrode being typically between 1 mm and 5 mm with the longitudinal spacing from the active electrode being between 1 mm and 5 mm.

In effect, the electrode assembly is bipolar, with only one of the electrodes (30) actually extending to the distal end of the unit. This means that the return electrode, in normal circumstances, remains spaced from the tissue being treated and a current path exists between the two electrodes via the tissue and the conductive liquid which is in contact with the return electrode 36.

The conductive liquid 46 may be regarded, as far as the delivery of bipolar electrosurgical energy is concerned, as a low impedance extension of the tissue. Radio frequency currents produced by the generator 10 flow between the active electrode 30 and the return electrode 36 via the tissue 44 and the immersing conductive liquid 46. The particular electrode arrangement shown in FIG. 2 is most suitable for tissue desiccation.

The axial as well as radial separation between the electrodes avoids the small spacing of the conventional bipolar arrangement in which both electrodes are tissue-contacting. As a result, there is less danger of unwanted arcing across the insulation surface, which allows comparatively high power dissipation for desiccation treatment, and, in the case of tissue cutting or vaporisation, prevents excessive arcing which can lead to interelectrode insulation damage.

The immersing saline solution may be provided from a conduit (not shown) forming part of the instrument 12. Thus, the invention may take the form of an electrosurgical system for the treatment of tissue immersed in a conductive fluid medium, comprising an electrosurgical instrument having a handpiece and an instrument shaft, and, on the end of the shaft, an electrode assembly, the assembly comprising a tissue contact electrode which is exposed at the extreme distal end of the instrument, and a return electrode which is electrically insulated from the tissue contact electrode and has a fluid contact surface spaced proximally from the exposed part of the tissue contact electrode, the system further comprising a radio frequency generator coupled to the electrode assembly of the instrument, a reservoir of electrically conductive fluid, such as the normal saline solution, and a conduit, typically and integral part of an endoscope, for delivering the liquid from the reservoir to the region of the electrode assembly. Pressure for delivering the liquid may be provided by a pump forming part of the apparatus.

Since in this embodiment of electrode assembly 28, the active electrode 30 is made of stainless steel filaments in the form of a brush, the electrode is flexible, providing a reproducible tissue effect which is comparatively independent of the application angle of the electrode to the tissue surface. The flexibility of the electrode 30 also results in a differential contact area of the active electrode dependent on the applied pressure, allowing variations in the breadth of desiccation over the surface of the tissue, reducing procedure time.

Desiccation occurs by virtue of radio frequency currents passing between the active electrode 30 and the conductive liquid 46 via the outer layer of the tissue 44 immediately beneath and in an area surrounding the active electrode 30. The output impedance of the generator is set at a level commensurate with the load impedance of the electrode assembly when used as shown in FIG. 2 with both electrodes in contact with the conductive liquid 46. In order to sustain this matched state for tissue desiccation, the output power of the generator is automatically controlled in a manner which will be described below so that vapour bubbles of significant size are substantially prevented from appearing at the active electrode 30, thereby avoiding a consequent increase in load impedance. In this way, the active electrode can be continually wetted by the conductive liquid so that, whilst the tissue water is removed by thermal desiccation, the impedance reaches an upper limit corresponding to the point at which the conductive liquid starts to boil. As a result, the system is able to deliver high power levels for desiccation without unwanted conductive liquid vaporisation leading to unwanted tissue effects.

Figure 3:
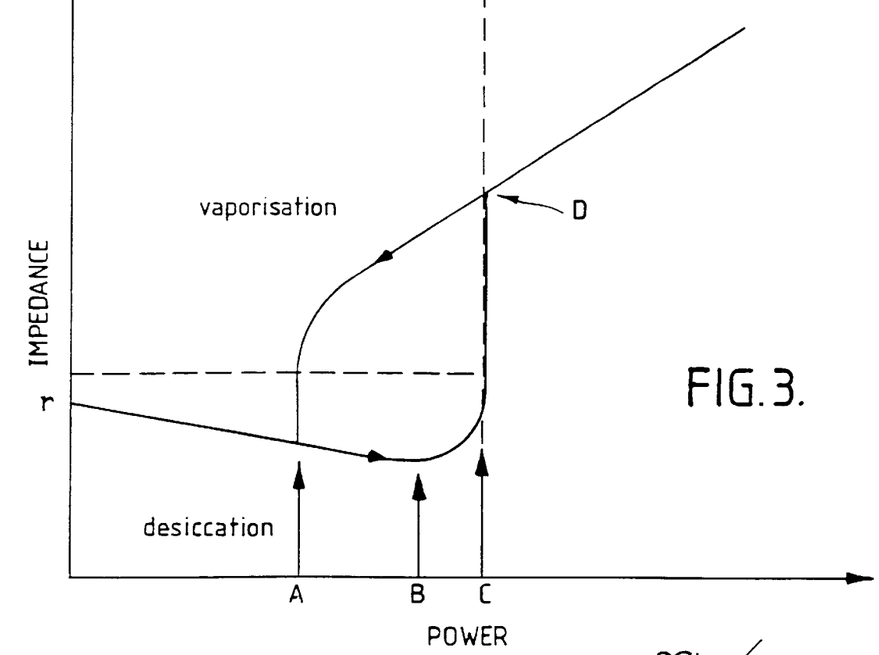
FIG. 3 is a load characteristic graph illustrating the variation in load impedance produced by an electrode assembly such as that shown in FIG. 2 when used in a conductive liquid, according to the delivered output power.

The electrical behaviour of the electrode assembly when the electrodes 30 and 36 are immersed in the conductive liquid 46 is now considered with reference to the graph of FIG. 3.

When power is first applied, there is presented to the generator an initial load impedance r which is governed by the geometry of the electrode and the electrical conductivity of the conductive liquid. The value of r changes when the active electrode touches the tissue. The higher the value of r, the greater is the propensity of the conductive liquid to vaporise. As power is dissipated in the tissue and the conductive liquid, the conductive liquid increases in temperature. In the case of normal saline, the temperature coefficient of conductivity is positive and the corresponding impedance coefficient is therefore negative so that the impedance initially falls. Thus, the curve in FIG. 3 indicates a fall in load impedance as the delivered power is increased, the impedance falling through point A to a minimum at point B, at which point saline in immediate contact with the electrode reaches boiling point. Small vapour bubbles now form on the surface of the active electrode and the impedance starts to rise as shown by the curve rising from point B to point C. Thus, once the boiling point has been reached, the arrangement displays a dominant positive power coefficient of impedance.

As the vapour bubbles form, there is an increase in the power density at the remaining active electrode to saline interface (the exposed area of the active electrode not covered by vapour bubbles) which further stresses the interface, producing more vapour bubbles and thus even higher power density. This is a runaway condition, with an equilibrium point only occurring once the electrode is completely enveloped in vapour. Thus, for a given set of variables, there is a power threshold corresponding to point C at which this new equilibrium is reached.

In the light of the foregoing, it will be appreciated that the region between points B and C in FIG. 3 represents the upper limit of desiccation power which can be achieved.

Upon formation of an electrode-enveloping vapour pocket, the impedance elevates to about 1 kΩ, as shown by point D in FIG. 3, the actual impedance value depending on a number of system variables. The vapour is then sustained by discharges across the pocket between the active electrode and the vapour/saline interface.

Figure 4:
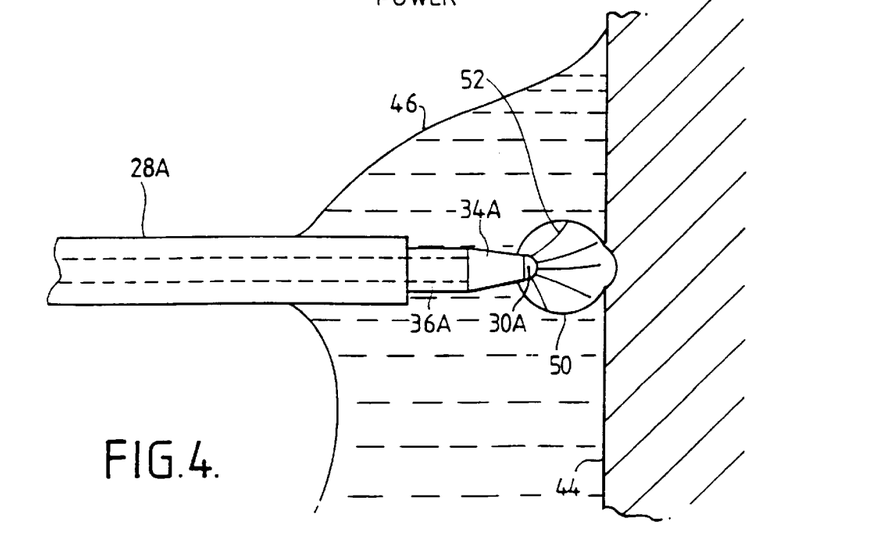
FIG. 4 is a fragmentary view of a second electrode assembly for tissue vaporisation, shown in use immersed in a liquid.

This state of affairs is illustrated by the diagram of FIG. 4 which shows an alternative electrode assembly 28A having a hemispherical or ball electrode 30A in place of the brush electrode 30 of the embodiment of FIG. 2. As before, the return electrode 36A is proximally spaced from the active electrode 30A by an intervening insulator 34A. The ball electrode is preferred for tissue vaporisation.

Once in the vaporisation equilibrium state, the vapour pocket, shown by the reference 50 in FIG. 4, is sustained by discharges 52 across the vapour pocket between the active electrode 30A and the vapour to saline interface. The majority of power dissipation occurs within this pocket with consequent heating of the active electrode. The amount of energy dissipation in this conduction is a function of the delivered power. It will be noted from FIG. 3 that the vaporisation mode, indicated by the dotted boundary lines, can be sustained at much lower power levels than are required to bring about formation of the vapour pocket. The impedance/power characteristic consequently displays hysteresis. Once the vaporisation mode has been established, it can be maintained over a comparatively wide range of power levels, as shown by the inclined part of the characteristic extending on both sides of point D. However, increasing the delivered output power beyond that represented by point D causes a rapid rise in electrode temperature, potentially damaging the electrode. To collapse the vapour pocket and to return to desiccation mode requires a significant power reduction back to point A, direct contact between the active electrode and the saline being reestablished and the impedance falling dramatically. The power density at the active electrode also falls so that the temperature of the saline now falls below boiling point and the electrode is then once again in a stable desiccation equilibrium.

The generator to be described hereinafter has the ability to sustain both the desiccation mode and the vaporisation mode. Whilst in general the electrode assemblies illustrated in FIGS. 2 and 4 can be used in either mode, the brush electrode of FIG. 2 is preferred for desiccation due to its wide potential area of coverage, and the ball electrode of FIG. 4 is preferred for vaporisation due to its small active electrode/return electrode surface area ratio. As can be seen from FIG. 4, tissue vaporisation occurs when the vapour pocket 50 intersects the tissue surface, with the electrode assembly preferably being held spaced above the tissue surface by a small distance (typically 1 mm to 5 mm).

The runaway condition which occurs when the delivered power reaches the level shown by point C in FIG. 3 is exacerbated if the generator has a significant output impedance, because the output voltage can then suddenly rise. With increased power dissipation and without the presence of the cooling liquid around the active electrode 30, the electrode temperature rises rapidly with consequent damage to the electrode. This also produces uncontrollable tissue disruption in place of the required desiccation. For this reason, the preferred generator has an output source impedance which, approximately at least matches the load impedance of the electrode structure when wetted.

The preferred generator now to be described allows both desiccation electrosurgery substantially without unwanted cell disruption, and electrosurgical cutting or vaporisation substantially without electrode burning. Although intended primarily for operation in a conductive liquid distension medium, it has application in other electrosurgical procedures, e.g. in the presence of a gaseous distension medium, or wherever rapid load impedance changes can occur.

Figure 5:
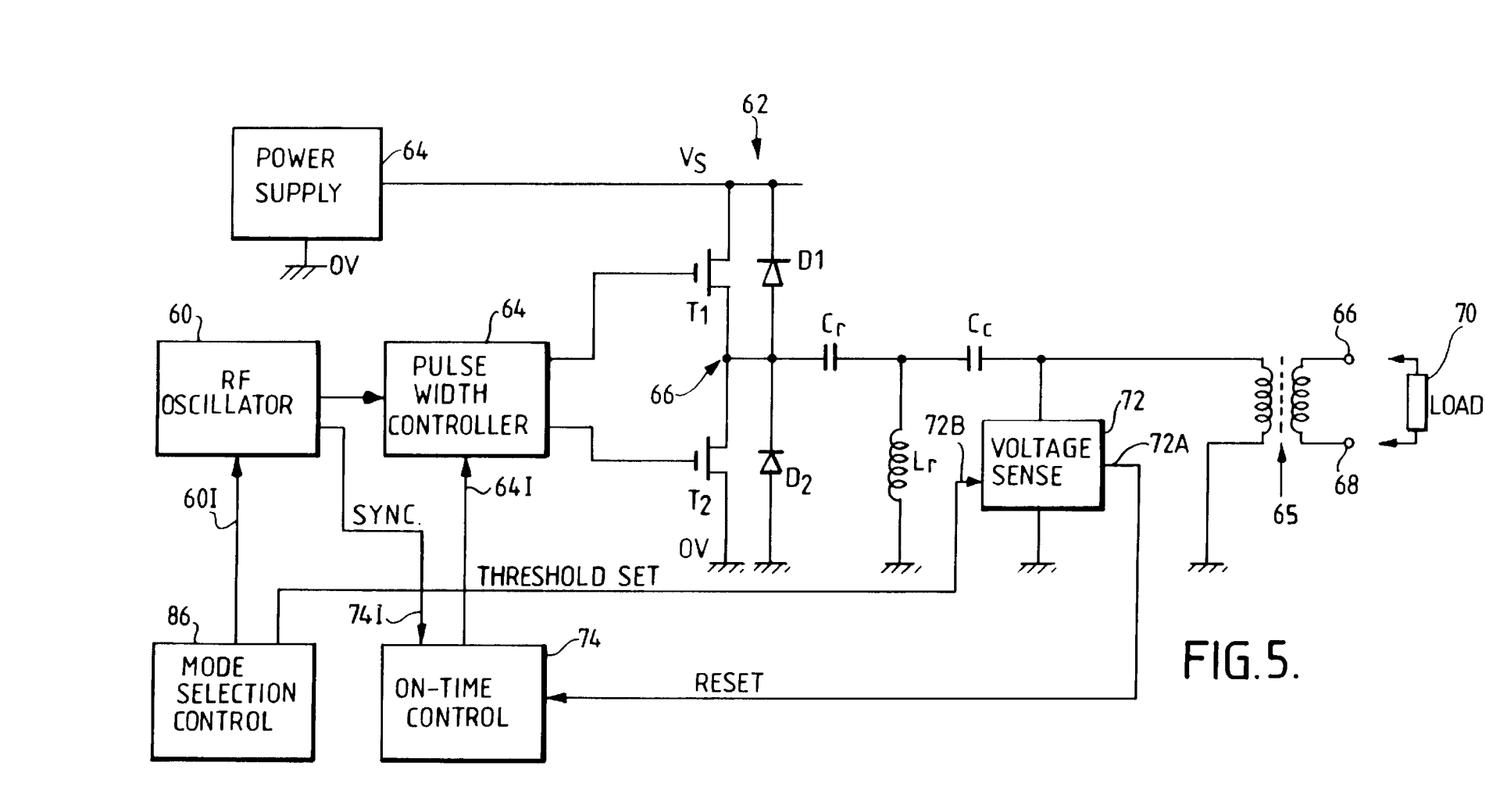
FIG. 5 is a combined circuit and block diagram of a generator in accordance with the invention.

Referring to FIG. 5, the generator comprises a radio frequency (RF) oscillator 60 which operates at above or below about 400 kHz, with any frequency from 300 kHz upwards into the HF range being feasible. Oscillator 60 drives a power output stage 62 comprising two power MOSFETs $T_1$, $T_2$ coupled in push-pull arrangement between two supply rails $V_S$ and 0V. The power supply rails are driven by a power supply stage 64.

Transistors $T_1$ and $T_2$ are driven in a switching mode by a pulse width controller 64 which is, itself, driven by the oscillator 60. Thus each transistor $T_1$, $T_2$ receives one gating pulse during each cycle of the RF oscillator 60, the pulses being timed such that $T_1$ is switched on during oscillator half cycles of one polarity, while $T_2$ is switched on during oscillator half cycles of the opposite polarity, and the width of the gating pulses is controlled according to the required output power.

Coupled to the junction between the two electronic switches represented by transistors $T_1$, $T_2$ is a series-resonant output circuit comprising a capacitor $C_r$ and an inductor $L_r$. The series resonant frequency of these two components is about 400 kHz, but generally different from the frequency of operation of oscillator 60. Coupled to the junction between capacitor $C_r$ and inductor $L_r$ via a coupling capacitor $C_c$ is one of end of a primary winding of an output isolation transformer 65 feeding the output terminals 66, 68 of the generator. The other end of the primary winding is coupled to one of the supply rails, in this case the ground connection 0V. Coupling capacitor $C_c$ is smaller than capacitor $C_r$.

The connection of the series-resonant circuit $C_r$, $L_r$ to the switches is direct; there is no intervening second series resonant circuit such as a parallel-resonant circuit, and the load impedance presented to the switches (when its variation is considered with respect to excitation frequency) exhibits a predominant minimum at the resonant frequency of the series-resonant circuit.

In parallel with the source and drain connections of each transistor $T_1$, $T_2$ is a respective energy recovery diode $D_1$, $D_2$.

Figure 6:
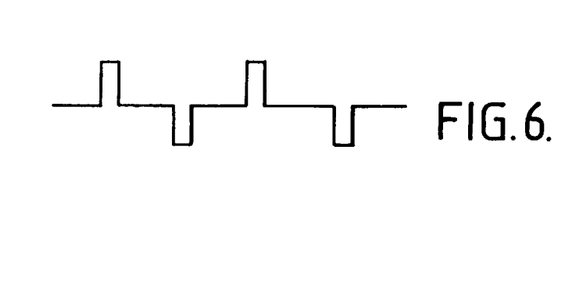
FIG. 6 is a waveform diagram.

Switching of transistors $T_1$, $T_2$ in the above-described manner causes the application to the junction 65 between the transistors of a RF excitation voltage having a waveform as shown in FIG. 6. A corresponding sinusoidal waveform is produced at the junction of the two series-resonant components $C_r$ and $L_r$ the amplitude of which depends on the difference in frequency between the oscillator frequency and the frequency of resonance, and on the impedance of the load 70 connected across the output terminals 66, 68.

Coupled across the output connections 66, 68 is a voltage threshold detector 72 having an output 72A coupled to an "on" time control circuit 74.

In operation of the generator, power is applied to the power supply 64 when electrosurgical power is demanded by the surgeon operating an activation switch arrangement which may be provided on a handpiece or footswitch (see FIG. 1). A constant output voltage threshold is set independently of the supply voltage via input 72B according to control settings on the front panel of the generator (see FIG. 1). Typically, for desiccation or coagulation the threshold is set at a desiccation threshold value between 150 volts and 200 volts. When a cutting or vaporisation output is required, the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved.

When the generator is first activated, the status of the control input 64I of the pulse width controller 64 (which is connected to the "on" time control circuit 74) is "on", such that the transistors T1, T2 which form the output stage 62 are each switched on for a maximum conduction period during each oscillation cycle which may be a full half cycle of the oscillator output. Providing the delivered power is sufficiently high, the temperature of the liquid medium surrounding the electrodes of the electrosurgical instrument (or within a gaseous medium, the temperature of liquids contained within the tissue) may rise to such an extent that the liquid medium vaporises, leading to a rapid increase in load impedance and a consequent rapid increase in the applied output voltage across terminals 12. This is an undesirable state of affairs if a desiccation output is required. For this reason, the voltage threshold for a desiccation output is set to cause a trigger signal to be sent to the "on" time control circuit 74 when the threshold is reached. The "on" time control circuit 74 has the effect of virtually instantaneously reducing the width of the gating pulses produced by controller 64 thereby virtually instantaneously reducing the "on" time of the RF switching device $T_1$, $T_2$.

Figure 7:
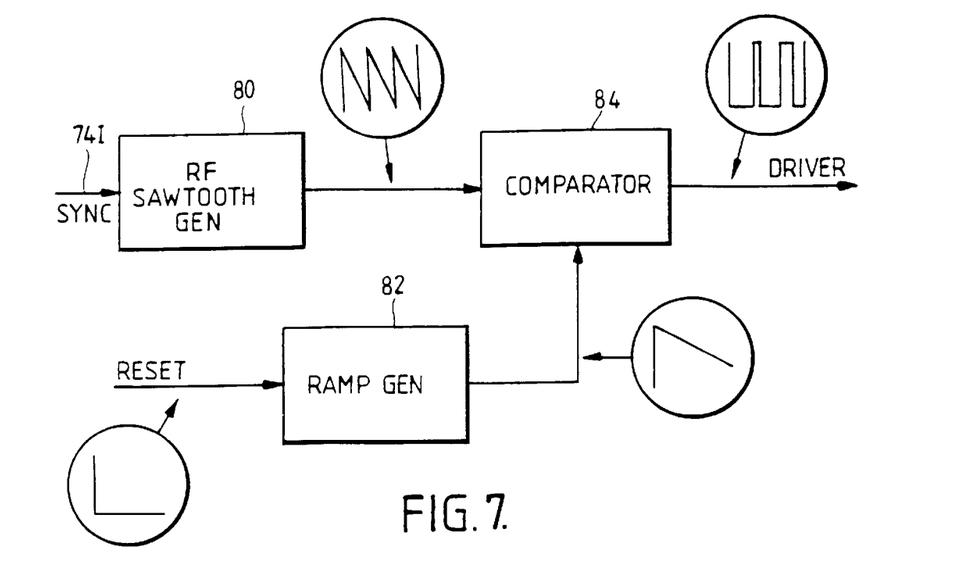
FIG. 7 is a block diagram of part of the control circuitry of the generator of FIG. 5.

Subsequent control of the "on" time of the devices $T_1$, $T_2$ in individual cycles of the oscillator 60 will be understood by considering the internal configuration of the "on" time control circuit 74 which is shown in FIG. 7. The circuit comprises an RF sawtooth generator 80 (synchronised at the RF oscillation frequency by a synchronisation signal derived from the oscillator and applied to a synchronisation input 74I), and a ramp generator 82 which is reset by a reset pulse from the output 72B of the voltage threshold detector 72 (see FIG. 5) produced when the set threshold voltage is reached. This reset pulse is the trigger signal referred to above. The "on" time control circuit 74 further comprises a comparator 84 for comparing the sawtooth and ramp voltages produced by the sawtooth and ramp generators 80 and 82 to yield a square wave control signal for application to the input 64I of the pulse width controller 64. As shown by the waveform diagrams in FIG. 7, the nature of the sawtooth and ramp waveforms is such that the mark-to-space ratio of the square wave signal applied to the controller 64 progressively increases after each reset pulse. As a result, after a virtually instantaneous reduction in "on" time on detection of the output voltage reaching the set voltage threshold, the "on" time of the RF oscillator is progressively increased back to the original maximum value. This cycle is continuously repeated until the temperature of the liquid surrounding the electrodes reduces to such a level such that vaporisation no longer occurs.

The output voltage of the generator is important to the mode of operation. In fact, the output modes are defined purely by output voltage, specifically the peak output voltage. The absolute measure of output voltage is only necessary for multiple term control. However, a simple single term control (i.e. using one control variable) can be used in this generator in order to confine the output voltage to predetermined limit voltages. Thus, the voltage threshold detector 72 shown in FIG. 5 compares the RF peak output voltage with a preset DC threshold level, and has a sufficiently fast response time to produce a reset pulse for the "on" time control circuit 74 within one RF half cycle.

When the series-resonant output circuit is excited by switching of transistors $T_1$, $T_2$ at a frequency near resonance, the amplitude of the voltage at the junction between transistors $T_1$, $T_2$ can exceed the supply voltage. In this condition, when both transistors are turned off, diodes $D_1$, $D_2$ recover energy from the resonance circuit into the supply. Intermediate levels of excitation are possible by using less than half-wave switching of the push-pull devices, the on-time providing excitation, the off-time providing power recovery and damping.

Before considering the operation of the generator further, it is appropriate to refer back to the impedance/power characteristic of FIG. 3. It will be appreciated that the most critical control threshold is that applicable during desiccation. Since vapour bubbles forming at the active electrode are non-conducting, the saline remaining in contact with the electrode has a higher power density and consequently an even greater propensity to form vapour. This degree of instability brings about a transition to a vaporisation mode with the same power level due to the runaway increase in power density at the active electrode. As a result, the impedance local to the active electrode rises. Maximum absorbed power coincides with the electrode condition existing immediately before formation of vapour bubbles, since this coincides with maximum power distribution and the greatest wetted electrode area. It is therefore desirable that the electrode remains in its wetted state for the maximum desiccation power. Use of voltage limit detection brings about a power reduction which allows the vapour bubbles to collapse which in turn increases the ability of the active electrode to absorb power. For this reason, the generator described in this specification includes a control loop having a large overshoot, in that the feedback stimulus of the peak voltage reaching the predefined threshold causes a large instantaneous reduction in power by causing a reduction in peak output voltage to a level significantly below the peak output voltage level set by the threshold detector 72. This control overshoot ensures a return to the required wetted state.

In the generator described above with reference to FIGS. 5, 6 and 7, power reduction in response to voltage threshold detection takes place through an instantaneous reduction in RF energy supplied to the series-resonant output circuit.

In the preferred embodiment, the instantaneous power reduction is by at least three quarters of available power (or at least half voltage) from the DC power supply and preferably by more. Thus, a high speed response is obtained in the RF stage itself.

In a typical desiccation episode the output voltage increases with increasing load impedance to a point at which the output voltage threshold is reached, whereupon the above-described instantaneous reduction in output stage "on" time occurs. This produces a rapid decrease in the RF output voltage, followed by a progressive increase, again as described above. When the output voltage again reaches the threshold voltage, the "on" time of the oscillator is once again instantly reduced and then progressively increased, so that the output voltage waveform repeats its previous pattern. Yet again, the threshold voltage is reached, again the output voltage is instantly reduced, and again the "on" time is allowed to increase, and so on until the conditions at the operation site change such that vapour is no longer formed.

It will be seen, then, that the control circuitry 74, 64 (FIG. 5) operates dynamically to control the output voltage both sufficiently rapidly and to a sufficient degree to maintain the voltage at a level consistent with, in this case, the level required for desiccation without tissue disruption due to arcing. The same technique can be used with a different threshold voltage to limit the output voltage to prevent electrode burning and/or excessive tissue vaporisation. In the latter case, the voltage limit may be set to a level between 250 volts (preferably 300 volts) and 600 volts.

Due to the high power density at the active electrode during the vaporisation mode, the great majority of delivered power is dissipated in the proximity of the electrode. In the vaporisation mode, it is desirable that a minimum of saline heating occurs, but that any tissue which encroaches the vapour boundary of the active electrode is vaporised. In the vaporisation mode, the vapour is sustained by arcs within the vapour pocket as described above with reference to FIG. 4. Increasing the output voltage during vaporisation results in increased volume of tissue removal due to the increased size of the vapour pocket. Collapse of the vapour pocket during tissue vaporisation has greater consequence, due to the increased necrosis as a result of the greater power dissipation in the surrounding saline. Vapour pocket collapse can be prevented by, firstly, arranging for the electrode impedance in vaporisation mode to be such that the instrument is in an unmatched condition as regards impedance, with result that the resonant output circuit Q is high and the output voltage does not change so rapidly as with lower load impedances and, secondly, the active electrode has a significant heat capacity that sustains the vapour pocket for a significant period.

An unwanted increased in the size of the vapour pocket can be prevented by limiting the peak output voltage during the vaporisation mode, which may be conveniently carried out by substituting a different threshold value for the voltage threshold detector 72 (see FIG. 5) when in the vaporisation mode.

The circuitry of the voltage threshold detector 72, and "on" time control circuit 74 (shown in FIG. 5) in the preferred generator in accordance with the invention is as described and shown in our co-pending European Patent Application No. 96304558.8.

Figure 8:
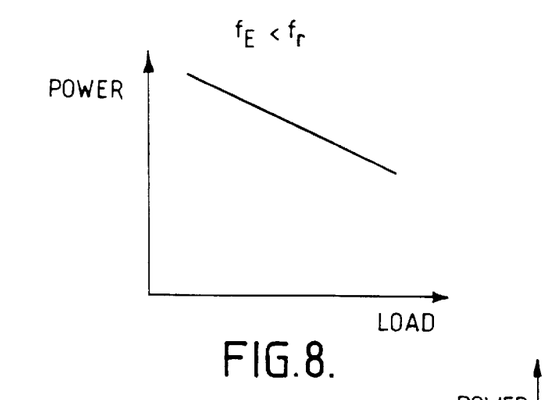
FIG. 8 is a power v. load impedance graph relating to the generator when operating in a desiccation mode.
Figure 9:
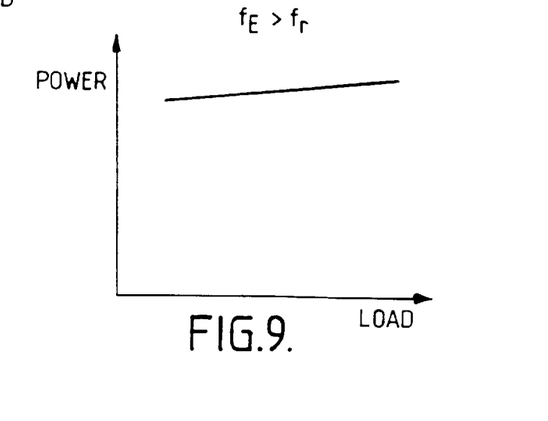
FIG. 9 is a similar graph applicable to a tissue cutting or vaporisation mode.

As has been described above, different threshold voltages are applicable to desiccation on the one hand and cutting or tissue vaporisation on the other hand. Accordingly, the generator includes a mode selection control 86, as shown in FIG. 5. In practice, this may be part of a microprocessor control system (not shown) producing outputs which depend on handpiece or foot-operated switch settings. Thus, for a desiccation output, the mode selection control sets the voltage threshold of threshold detector 76 to a first value via input 72B, whilst for cutting or vaporisation, a different, higher threshold value is set. Improved results can also be obtained by setting the RF oscillator frequency to different values according to whether desiccation or cutting/vaporisation are required. Thus, for desiccation, the mode selection control applies a frequency control signal to the RF oscillator via control input 60I to set the oscillator frequency below the resonant frequency of the series-resonant combination $C_r$, $L_r$. Conversely, when cutting or tissue vaporisation is required, the RF oscillator is set to a frequency higher than the resonant frequency. The lower frequency has the effect of skewing the power versus load impedance characteristic so as to increase the power available at low impedances, as encountered during desiccation. The higher oscillator frequency has the effect of flattening the power versus load impedance curve, favouring higher impedances, as encountered when the immersing fluid vaporises. These power/load impedance variations are shown diagrammatically in FIGS. 8 and 9, in which $f_E$ and $f_r$ represent the excitation (i.e. oscillator) frequency and the resonant frequency respectively.

Blended modes can be used by constantly alternating between desiccation and cut states or by altering the position of the thresholds.

Figure 10:
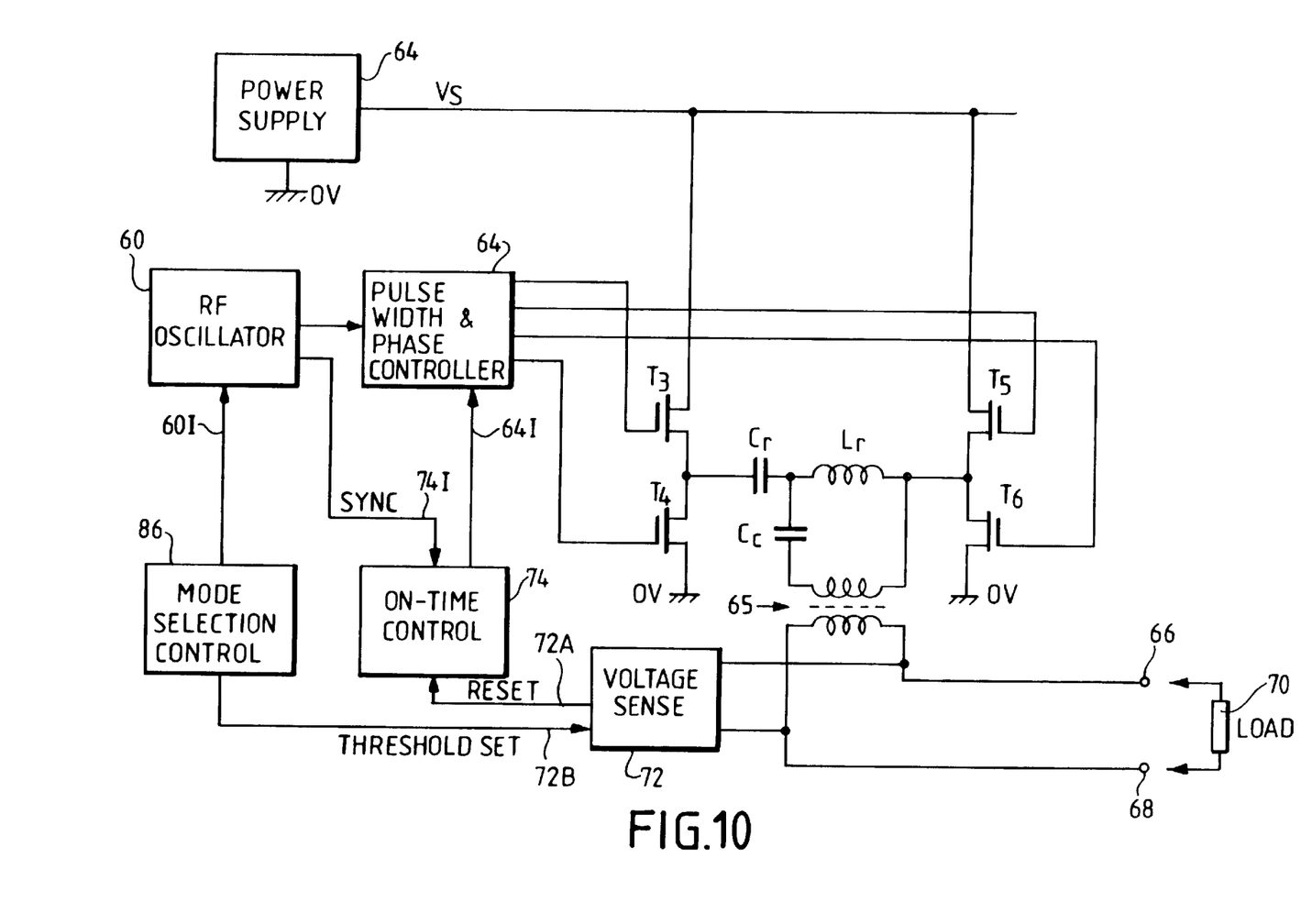
FIG. 10 is a combined circuit and block diagram of an alternative generator in accordance with the invention.

An alternative generator to that described above with reference to FIG. 5 may be used, having an output stage with switching means in bridge configuration, as shown in FIG. 10. In this case, the switching devices comprise four power MOSFETs arranged in two pairs of two transistors, each pair being arranged in a push-pull configuration. The first pair is shown in FIG. 10 as transistors T3 and T4, and the second pair as transistors T5 and T6. The series-resonant output circuit comprising capacitor $C_r$ and conductor $L_r$ is coupled between the respective junctions of the two pull-push pairs T3, T4 and T5, T6 so that when these pairs are driven in phase opposition by a pulse width and phase controller circuit 64, the radio frequency power signal is applied across the series-combination $C_r$, $L_r$. As in the generator of FIG. 5, the output to an electrosurgical instrument is taken from across the inductor $L_r$ via a coupling capacitor $C_c$ and an isolation transformer 65, the transformed radio frequency output voltage appearing at terminals 66, 68 for connection of an electrosurgical load 70. In other respects, this alternative generator is similar to the generator described above with reference to FIG. 5, and common reference numerals for the common parts are used in FIGS. 10 and 5 respectively. The voltage waveform generated across the series-resonant circuit $C_r$, $L_r$ typically has the same waveform as that developed by the generator of FIG. 5, i.e. as shown in FIG. 6. However, in the case of this alternative generator, by incorporating a phase control function in the circuit 64 driving the switching transistors T3 to T6, the phase difference between the drive signals applied to the respective pairs T3, T4, and T5, T6 can be varied from the maximum value of 180° downwards so that the output power is reduced. This constitutes an additional variable for varying output power. Indeed, when required, the phase difference can be reduced to such an extent that the output power is zero, which means that, for example, the supply voltage $V_S$ obtained from power supply 64 can be maintained constant at all times rather than being used as a secondary means of power reduction.

To summarise, then, the bridge configuration allows rapid power reduction to be achieved when the conductive liquid surrounding the instrument electrodes vaporises not only by reducing the "ON" time of the transistors, but also by varying the relative phase between the two transistor pairs downwards from 180°. It is also possible to alter the excitation frequency of RF oscillator 60 so as to be further from the resonant frequency defined by the series-combination of capacitor $C_r$ and inductor $L_r$ as an additional means of reducing output power.

From a general viewpoint, a radio frequency generator for an electrosurgical system is provided, the system including an electrode assembly having two electrodes for use immersed in an electrically conductive fluid. The generator has control circuitry for rapidly reducing the delivered radio frequency output power by at least 50% within at most a few cycles of the peak radio frequency output voltage reaching a predetermined threshold limit. In this way, tissue coagulation can be performed in, for example, saline without significant steam generation. The same peak voltage limitation technique can be used in a tissue vaporisation or cutting mode to limit the size of the steam pocket at the electrodes and to avoid electrode burning. The generator has a push-pull output stage with a series-resonant output circuit, the output stage being driven by a radio frequency oscillator at a frequency which, in general, differs from the resonant frequency of the resonant output circuit. Power control is achieved by varying the ON-time of switching transistors forming the push-pull output pair and by altering the frequency spacing between the excitation frequency and the resonant frequency of the series-resonant output circuit. In an alternative embodiment, a bridge configuration using two push-pull pairs is used, yielding a further power control variable: the relative phase of the driving signals to the respective transistor pairs.

What is claimed is:

1. An electrosurgical generator for supplying radio frequency power to an electrical instrument, the generator comprising a radio frequency output stage having at least a pair of electrosurgical output lines for the delivery of radio frequency power to the instrument, a power supply coupled to the output stage for supplying power to the output stage, and control circuitry including sensing means for deriving a sensing signal representative of the radio frequency peak output voltage developed across the output lines, wherein the output stage comprises a series-resonant output circuit coupled to the output lines and switching means coupled to the resonant output circuit, and wherein the control circuitry is operable to vary the switching intervals of the switching means to reduce the delivered radio frequency power in response to a predetermined condition of the sensing signal.

2. A generator according to claim 1, wherein the series-resonant output circuit comprises the series combination of an inductance and a capacitance, and is coupled to the switching means such that a switched radio frequency output waveform is developed across the series combination, the output lines of the generator being coupled to the series-resonant circuit to receive the radio frequency voltage developed across the inductance or the capacitance.

3. A generator according to claim 2, wherein the output lines are coupled to receive the radio frequency voltage developed across the inductance.

4. A generator according to claim 2, wherein the series combination is coupled between the switching means and a ground connection or one of a pair of supply rails of the power supply means, one of the output lines of the generator being coupled to a junction between the inductance and the capacitance.

5. A generator according to claim 4, wherein the capacitance is connected between the switching means and the junction, and the inductance is coupled between the junction and the ground connection on the said one supply rail.

6. A generator according to claim 2 or claim 3, wherein the switching means comprise semiconductor switching devices connected in a bridge configuration, the series combination being coupled between oppositely phased nodes of the switching means.

7. A generator according to claim 2, including a series-connected coupling capacitance coupled in a signal path between the series-resonant circuit and one of the output lines.

8. A generator according to claim 7, wherein the coupling capacitance is of a smaller value than the capacitance of the series-resonant combination.

9. A generator according to claim 1, wherein the switching means comprise a pair of electronic switches connected in a push-pull series arrangement between a pair of supply rails of the power supply, the series resonant output circuit being coupled to the connection between the electronic switches.

10. A generator according to claim 9, wherein the switching means comprise two pairs of electronic switches in a bridge configuration, each pair connected in a push-pull series arrangement between the supply rails, the series-resonant output circuit being coupled between the connection between the switches of one pair and the connection between the switches of the other pair, the two pairs being arranged so as to be driven with opposite respective phases.

11. A generator according to claim 10, wherein the switching means are connected to switch current repeatedly through the resonant output circuit at a radio frequency, and wherein the control circuitry is so arranged and coupled to the switching means as to reduce the switching means radio frequency duty cycle sufficiently rapidly to cause at least a 50% reduction in delivered output power within 100 $\mu$s of a predetermined radio frequency peak output voltage threshold having been reached and wherein the control circuitry is arranged to drive each of the electronic switches so as to perform partial cycle switching whereby each has a variable on-time during respective radio frequency cycles, the on-time of both switches being controllable sufficiently rapidly to effect the said at least 50% power reduction within 5 radio frequency cycles.

12. A generator according to claim 9, wherein the switching means are connected to switch current repeatedly through the resonant output circuit at a radio frequency, and wherein the control circuitry is so arranged and coupled to the switching means as to reduce the switching means radio frequency duty cycle sufficiently rapidly to cause at least a 50% reduction in delivered output power within 100 $\mu$s of a predetermined radio frequency peak output voltage threshold having been reached and wherein the control circuitry is arranged to drive each of the electronic switches so as to perform partial cycle switching whereby each has a variable on-time during respective radio frequency cycles, the on-time of both switches being controllable sufficiently rapidly to effect the said at least 50% power reduction within 5 radio frequency cycles.

13. A generator according to claim 1, wherein the switching means are connected to switch current repeatedly through the resonant output circuit at a radio frequency, and wherein the control circuitry is so arranged and coupled to the switching means as to reduce the switching means radio frequency duty cycle sufficiently rapidly to cause at least a 50% reduction in delivered output power within 100 $\mu$s of a predetermined radio frequency peak output voltage threshold having been reached.

14. A generator according to claim 13, wherein the control circuitry includes a driver stage including a ramp generator operable to cause a control signal to be applied to the drive stage initially to reduce the said radio frequency duty cycle to cause the at least 50% reduction in power delivered via the output lines, and then progressively to increase the duty cycle at a less rapid rate until the sensing signal indicates that the predetermined voltage threshold has once again been reached.

15. A generator according to claim 1, further including an oscillator for driving the switching means, the oscillator being operable at a frequency which is different from the resonant frequency of the series resonant combination.

16. A generator according to claim 15, including a series-connected coupling capacitance coupled in a signal path between the series-resonant circuit and one of the output lines, and wherein the values of the coupling capacitance and the components of the series-resonant circuit are such that the difference between the oscillator frequency and the resonant frequency is between $\frac{1}{4}(C_c f_r/C_r)$ and $(C_c f/C_r)$, where $C_c$ is the coupling capacitance, $C_r$ is the capacitance element of the series-resonant circuit and $f_r$ is the resonant frequency.

17. An electrosurgical system including a generator for generating radio frequency power and an electrosurgical instrument having at least one electrode for use immersed in a conductive liquid, wherein the generator comprises an output stage including at least one radio frequency power device, a series-resonant output circuit, and at least a pair of output connections arranged to receive radio frequency power from the power device, one of the pair of connections being connected to the said electrode, and wherein the generator further comprises a control stage operable to reduce the conduction time of the power device during individual radio frequency cycles in response to a sensing signal representative of the peak output voltage across the output connections exceeding a predetermined sensing signal threshold value, whereby the radio frequency power delivered to the electrode structure is rapidly reduced when the conductive liquid is vaporised.

18. A system according to claim 17, wherein the electrode structure includes a projecting treatment electrode and a liquid contact electrode spaced from the treatment electrode, both electrodes being for use surrounded by the conductive liquid and each being connected to a respective one of the pair of output connections, the control stage being operable to reduce the conduction time of the power device when the conductive liquid at the treatment electrode is vaporised thereby to cause the collapse of vapour bubbles at the treatment electrode and a decrease in the electrical load impedance.

19. A system according to claim 18, wherein the electrosurgical instrument has an electrode structure having juxtaposed first and second electrodes for immersion in a conductive liquid, the first and second electrodes respectively forming a tissue contact electrode at an extreme distal end of the instrument and a return electrode proximally spaced from the tissue contact electrode.

20. A system according to claim 18, wherein series-resonant circuit coupled between the power device and the output connections has a resonant frequency which is different from the frequency of operation of the generator.

21. A system according to claim 20, wherein the first and second values are in the ranges of from 150V to 200V and from 250V to 600V respectively, the voltages being peak voltages.

22. A system according to claim 17 and operable in at least a tissue desiccation mode and a tissue cutting or vaporisation mode, wherein the generator includes a mode selection control, and wherein the control stage is operable automatically to adjust the radio frequency power supplied to the electrode structure to limit the peak generator output voltage to a first value when the desiccation mode is selected and to at least one second value when the cutting or vaporisation mode is selected, the second value or values being higher than the first value.

23. A system according to claim 17, operable in at least a tissue desiccation mode and a tissue cutting or vaporisation mode and having a radio frequency oscillator for driving the power device, wherein the generator includes a mode selection control coupled to the oscillator for adjusting the oscillator frequency of the oscillator so as to be higher than the resonant frequency of the series resonant output circuit in the cutting or vaporisation mode and lower than the said resonant frequency in the desiccation mode.

24. An electrosurgical generator for supplying radio frequency power to an electrosurgical instrument, the generator comprising a radio frequency output stage having at least a pair of electrosurgical output connections for the delivery of radio frequency power to the instrument, a radio frequency oscillator for feeding a radio frequency signal to the output stage, and control circuitry including sensing means for deriving a sensing signal representative of the radio frequency signal delivered from the output connections, wherein the output stage comprises a series-resonant output circuit coupled to the output connections, the resonant frequency of the series-resonant output circuit being different from the operation frequency of the oscillator, and wherein the control circuitry provides a feedback signal for controlling the delivered radio frequency power.

25. A generator according to claim 24, wherein the output stage is a push-pull output stage, and the control circuitry is operable to alter the on-time of one or more semiconductor devices forming part of the output stage independently of the frequency of operation.

26. A generator according to claim 24, wherein the sensing means is arranged to derive a sensing signal representative of the radio frequency peak output voltage developed across the output connections.

* * * * *